(12) United States Patent
Kolb et al.

(10) Patent No.: US 7,167,097 B2
(45) Date of Patent: Jan. 23, 2007

(54) BLOOD DONATION DEVICE

(75) Inventors: Stefan Kolb, Oberursel (DE); Artur Meisberger, St. Wendel (DE)

(73) Assignee: Fresenius HemoCare Beteiligungs GmbH, Bad Homburg (DE)

( * ) Notice: Subject to any disclaimer, the term of this patent is extended or adjusted under 35 U.S.C. 154(b) by 0 days.

(21) Appl. No.: 10/253,885

(22) Filed: Sep. 25, 2002

(65) Prior Publication Data

US 2003/0069562 A1 Apr. 10, 2003

(30) Foreign Application Priority Data

Sep. 25, 2001 (DE) ................................ 101 47 208

(51) Int. Cl.
G08B 21/00 (2006.01)

(52) U.S. Cl. .................. 340/613; 340/606; 340/573.1; 340/691.1; 340/691.6; 600/573; 600/584; 604/403; 604/404

(58) Field of Classification Search ............... 340/613, 340/606, 573.1, 693.5, 691.1, 691.6; 600/573, 600/562, 584; 604/403, 404, 409
See application file for complete search history.

(56) References Cited

U.S. PATENT DOCUMENTS

| | | | | |
|---|---|---|---|---|
| 4,390,073 A | | 6/1983 | Rosen | ........................ 177/118 |
| 4,481,827 A | * | 11/1984 | Bilstad et al. | ................. 73/861 |
| 4,601,355 A | | 7/1986 | Takahashi | ........................ 177/2 |
| 5,439,460 A | * | 8/1995 | Hoover | ........................ 604/403 |
| 5,584,320 A | * | 12/1996 | Skinkle et al. | .......... 137/565.12 |
| 5,624,185 A | | 4/1997 | Whisson | ...................... 366/141 |
| 5,989,177 A | * | 11/1999 | West et al. | .................... 494/46 |
| 6,113,554 A | * | 9/2000 | Gilcher et al. | .............. 600/573 |
| 6,402,702 B1 | * | 6/2002 | Gilcher et al. | .............. 600/573 |
| 2003/0138346 A1 | * | 7/2003 | Gunn et al. | .................... 422/24 |
| 2004/0165348 A1 | * | 8/2004 | Clark et al. | ................. 361/686 |

FOREIGN PATENT DOCUMENTS

| | | |
|---|---|---|
| DE | 37 37 304 | 5/1989 |
| DE | 3737304 | 5/1989 |
| DE | 43 33 266 A1 | 3/1995 |
| DE | 37 51 436 T2 | 4/1996 |
| DE | 29611131 | 10/1996 |
| FR | 2 574 540 | 6/1986 |
| FR | 2 796 182 | 1/2001 |
| WO | WO 88/02641 | 4/1988 |
| WO | WO 99/25397 | 5/1999 |

* cited by examiner

*Primary Examiner*—Julie Lieu
(74) *Attorney, Agent, or Firm*—Jacobson Holman PLLC

(57) ABSTRACT

A blood donation device with a receptacle for a blood donation container and a control section at which utensils required by the operator can be accommodated and/or by means of which parameters of the donation process can be varied, detected and/or retrieved. Bending of the operator to the blood donation device is avoided by the fact that the control section is arranged in an elevated position with respect to the receptacle of the blood donation device.

19 Claims, 1 Drawing Sheet

BLOOD DONATION DEVICE

BACKGROUND OF THE INVENTION

1. Field of the Invention

The present invention relates to a blood donation device with a receptacle for a blood donation container and a control section at which utensils required by the operator can be accommodated and/or by means of which parameters of the donation process can be varied, detected and/or retrieved.

2. Description of the Related Art

A blood donation device having a weighing unit with scales and a control section by means of which parameters of the donation process can be varied is known, for example, from DE 37 37 304 C2. This specification discloses a normal blood donation device in which the donor blood is collected in a collection bag. The collection bag lies on the weighing scales of an electronic weighing unit which serve as a receptacle. The blood is led from the donor into the collection bag via a supply hose running through a pinch valve. The pinch valve can be activated by the blood donation device so that the blood donation process can be interrupted or the blood flow can be restricted when corresponding predetermined values such as the quantity of blood or the blood donation time are reached.

The weighing scales which serve as a receptacle for a blood donation container, especially a blood bag, project upwards from the casing of the blood donation device and are connected to a corresponding weighing device or a swivelling device via a shaft extending from the casing. At the front of the blood donation device disclosed in DE 37 37 304 C2 there is located a weight indicator, a level control and a keyboard. This keyboard can be used to switch the device on and off, interrupt the donation process, initiate weighing and calibrate the device.

Scales with control panels are known in numerous different applications, such as, for example, determining the weight of foodstuffs. Such a device is disclosed in U.S. Pat. No. 4,601,355. The apparatus shown there is provided with a separate control section whose keyboard can be used to retrieve stored data and by means of which the weighing process can be simplified. This control section can be removed from the casing of the scales if required.

In blood donation devices of the type specified initially, the blood from the donor flows as a result of gravity into the collection bag, which is usually positioned on weighing scales serving as the receptacle. For this reason, previously known blood donation devices are usually mounted on the floor or only slightly elevated.

This has the disadvantage that operation of the blood donation device is relatively complicated since the operator of the device must always bend to read out data, for example, or to change the operation.

It is thus the object of the present invention to further develop a blood donation device of the type specified initially so that operation of the device is simplified.

SUMMARY OF THE INVENTION

This object is achieved starting from a generic blood donation device by arranging the control section such that it is elevated with respect to the receptacle of the blood donor device. By this means frequent bending to determine or change the operating parameters becomes superfluous. Rather it is sufficient for the operator to face the elevated control section to take the required measures or read off the displays. The elevated arrangement of the control section also has the advantage that any lights arranged to indicate certain operating states are more easily identifiable. This is especially important since the operating staff usually need to monitor not just one device but a plurality of devices at the same time. This is substantially simplified by arranging the control section in an elevated position. For example, alarm states can be identified very much more quickly than with conventional blood donation devices.

The receptacle is usually connected to a measuring device, especially scales, to determine the quantity of donated blood. The measuring device can operate gravimetrically but also any other measuring method, such as for example volumetric determination of the quantity of donated blood can be used.

In a further development of the present invention it is provided that the control section has a keyboard whose keys are actuating devices for switching the device on and off, interrupting the blood donation process, activating and deactivating a swivel device, generating a display of the quantity of donated blood and/or the blood donation time still remaining and for calibration. It can also be provided that the control section only has the most important and frequently used keys while rarely used keys can be arranged on the casing of the blood donation device.

The control section can have a keyboard by means of which the device is programmable. For example, it can be provided that the duration of the donation process and/or the quantity of blood to be donated can be entered by means of the keyboard. For these processes according to the invention, there is also no need for the operator to bend but these data can be entered in a convenient position as a result of the control section being arranged in an elevated position.

It can also be provided that the control section has a display which displays information on the progress of the donation process to the donor. With the displays of previously known devices arranged on the floor, it was not possible for the donor to observe the progress of the donation process such as, for example, the quantity of blood donated so far or the time still remaining until the end of the donation process. On the control section there can also be provided an operator display which displays the data of the donation process to the operator.

The control section can have an indicator device by means of which the operating states of the device can be displayed. For example, it is feasible that alarms or the end of donation must be displayed. As a result of the elevated arrangement of the control section, the operating staff can easily identify from a greater distance that either an error function has occurred, for example, or the end of the donation process has been reached. Thus, the blood donation device according to the invention not only provides increased comfort but also increased safety since alarm states can quickly be detected.

The indicator device can be pulled out with respect to the control section such that the indicator device can be arranged in an elevated position with respect to the control section. In this way an especially clearly visible position of the indicator device can be achieved.

According to a further development of the present invention, it is provided that the control section has a keyboard and/or a display which can be removed from the control section. In this way, it is possible, for example, for the operator to remove the keyboard from the control section and take it directly in his/her hand to simplify the input or detection of operating values still further. The connection between the control section and the keyboard and/or display can be made by cable or also by infrared transmission etc.

The utensils required by the operator can comprise a barcode reader and welding tongs, whereby holders to accommodate this equipment are provided at the control section. The barcode reader is required, for example, to precisely identify the blood donation bag or a connector arranged thereon. The welding tongs are required to seal hoses at the end of the donation process.

In a preferred development of the present invention it is provided that the control section is arranged on a support extending vertically or running obliquely from a casing of the blood donation device.

It is especially advantageous if the support is arranged such that it can be swivelled with respect to the casing. In this way the control section can be suitably positioned.

It can also be provided that the control section is arranged movably with respect to the support. In this case, it is feasible that the display facing the donor can be swivelled so that this is as visible as possible. It is also feasible that the indicator device can be swivelled or twisted such that this can be seen especially clearly by the operating staff so that especially an alarm state can be quickly detected.

In a further development it is provided that the support can have a variable length. In this way, it can be achieved that the control section is always at the optimum height for persons of different height.

The support can be removable from the casing. According to this embodiment, the support is removable as a complete section and can be attached to the casing of the blood donation device as required and as comfortable.

It is especially advantageous if the support is connectable to the casing by a plug connection by means of which both the mechanical connection and the electronic contact can be made. In this way, by simply plugging the support into the casing or a suitable receptacle, it is possible to achieve mechanical fixing of the support and at the same time make the required electrical or electronic contacts.

BRIEF DESCRIPTION OF THE DRAWINGS

Further details and advantages of the present invention are explained in detail with reference to an embodiment shown in the drawings where.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
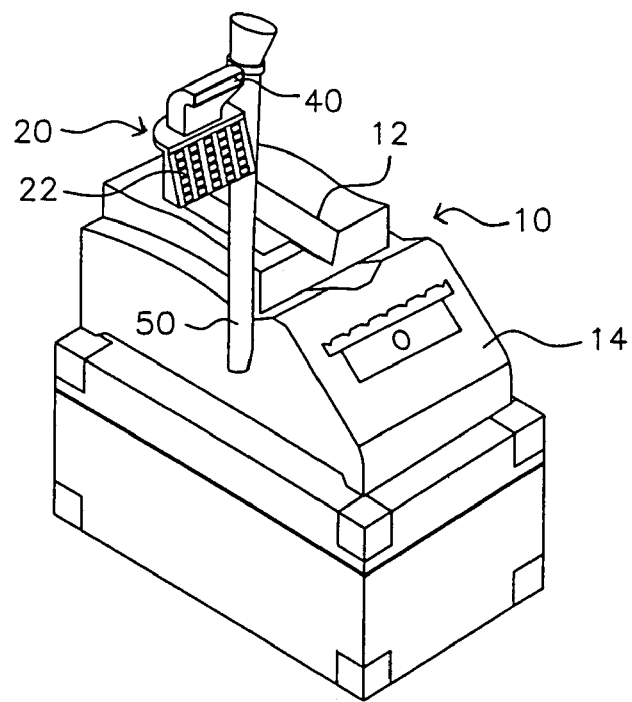
FIG. 1 is a perspective view of a blood donation device according to the present invention.

FIG. 1 shows in perspective view the blood donation device 10 which is arranged slightly elevated on a support positioned on the floor. The blood donation device 10 has a balance 12 in whose scales is inserted a collection bag for the blood donation. The blood donation device 10 has a casing 14. The balance 12 is arranged so that there is a drop between the blood donor and the collection bag.

The support 50 on which the control section 20 is arranged extends vertically from the casing. The support must not necessarily extend vertically but can also run obliquely upwards. The control section 20 has a holder for a barcode reader 40 and a keyboard 22. By means of the keyboard 22 the operator can modify parameters of the donation process at a suitable height, i.e. switch the device on or off, interrupt the donation process or generate displays or print out data or, for example, program the device. For this purpose the blood donation device has a control unit and a memory by means of which the corresponding sequence of the blood donation process is regulated.

The balance can also be calibrated by means of the keyboard 22 or a swivel device can be activated or deactivated.

Figure 2:
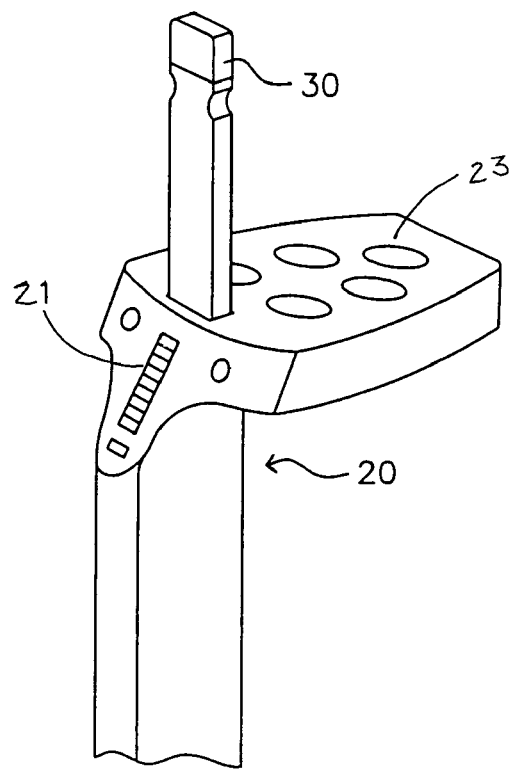
FIG. 2 is a perspective view of the control section with donor display, keyboard and extendible indicator unit according to a further embodiment of the present invention.

FIG. 2 shows a perspective view of another embodiment of the control section 20 with donor display 21 and operator display/keyboard 23 and with the extendible optical indicator device 30. The indicator device 30 has signal lights or a corresponding display by means of which specific operating states of the device, such as for example an alarm or the end of the blood donation process, can be clearly displayed visually. As a result of the elevated position of the indicator device 30, the operating staff can identify especially clearly whether such operating states exist.

The indicator device 30 can be extended telescopically with respect to the control section 20 and is shown in this state in FIG. 2. If this is not required, the indicator device 30 is pushed in.

In total, as a result of the blood donation device according to the invention, it is possible to significantly improve the operating comfort of the blood donation device as a result of the elevated position of the control section and also increase the safety for the blood donor since, for example, optical devices can also be provided in an elevated position which can immediately display to the operating staff and in a clearly visible position any faulty operating state or the end of the donation process.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A blood donation device comprising a receptacle for a blood donation container and a control section by which parameters of the donation process are varied, detected and/or retrieved, said control section being arranged on a support extending vertically or running obliquely from a casing of the blood donation device so as to be elevated as compared with the receptacle of the blood donation device, said elevated control section having an indicator for displaying an operating state of the device, said indicator being arranged in an elevated position with respect to the control section for increased visibility of said displayed operating state and including signal lights configured to emit a multi-directional visual indication of specific operating states of the device to operating staff, said device further including a donor display on said control section for displaying donation process progress information to said donor.

2. The blood donation device according to claim 1, wherein the control section has a keyboard having keys that are actuating devices for switching on and off the device, interrupting the blood donation process, activating and deactivating a swivel apparatus, generating a display of the quantity of donated blood and/or the blood donation time still remaining and for calibrating.

3. The blood donation device according to claim 1, wherein the control section has a keyboard by means of which the device is programmed.

4. The blood donation device according to claim 3, wherein a duration of the donation process and/or the quantity of blood to be donated are entered using the keyboard.

5. The blood donation device according to claim 1, wherein the control section has a second display configured to present data on the donation process to the operator.

6. The blood donation device according to claim 1, wherein the control section has a removable keyboard for handheld use.

7. The blood donation device according to claim 1, wherein the control section includes holders to accommodate utensils required by the operator that include a barcode reader and welding tongs.

8. The blood donation device according to claim 1, wherein the support is arranged to swivel with respect to the casing.

9. The blood donation device according to claim 1, wherein the control section is arranged to swivel with respect to the support.

10. The blood donation device according to claim 1, wherein the support is variable in length.

11. The blood donation device according to claim 1, wherein the support is removable from the casing, said support being connected to the casing by a plug connection by means of which both a mechanical connection and an electronic contact are made.

12. The blood donation device according to claim 1, wherein the control section has a removable display for handheld use.

13. A blood donation device comprising a casing having a receptacle for a blood donation container, and a control section by which parameters of the donation process are varied, detected and/or retrieved, said control section mounted on a support element so as to be elevated as compared with the receptacle of the blood donation device, said control section having an operator display for displaying donation process data to an operator, a donor display for displaying donation process progress information to said donor, and an optical indicator for visually displaying an operating state of the device, said indicator extending so as to be arranged in an elevated position with respect to the control section for increased visibility of said displayed operating state.

14. The blood donation device according to claim 13, wherein the control section has a removable display and keyboard for handheld use.

15. The blood donation device according to claim 13, wherein the support is connected to the casing by a plug connection that makes both a mechanical connection and an electronic contact.

16. The blood donation device according to claim 13, wherein the control section includes holders to accommodate utensils required by the operator that include a barcode reader and welding tongs.

17. The blood donation device according to claim 13, wherein said optical indicator includes signal lights configured to emit a multi-directional visual indication of specific device operating states.

18. A blood donation device comprising a casing having a receptacle for a blood donation container, and a control section by which parameters of the donation process are varied, detected and/or retrieved, said control section mounted on a support element so as to be elevated as compared with the receptacle of the blood donation device and having a donor display configured to display donation process progress information to said donor, said control section further having an optical indicator equipped with signal lights and arranged in an elevated position with respect to the control section for displaying various operating states of said device with increased visibility to operating staff.

19. The blood donation device according to claim 18, wherein said signal lights are configured to emit a multi-directional visual indication of specific device operating states.

* * * * *